(12) United States Patent
Wilkhu

(10) Patent No.: US 7,717,118 B2
(45) Date of Patent: May 18, 2010

(54) PROTECTIVE SHIELD

(75) Inventor: Harshdeep S. Wilkhu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 200 days.

(21) Appl. No.: 11/638,279

(22) Filed: Dec. 13, 2006

(65) Prior Publication Data

US 2007/0157936 A1    Jul. 12, 2007

Related U.S. Application Data

(60) Provisional application No. 60/749,819, filed on Dec. 13, 2005.

(51) Int. Cl.
*A61F 5/37* (2006.01)
*A61F 13/00* (2006.01)
*A61F 5/00* (2006.01)
*A47B 7/00* (2006.01)

(52) U.S. Cl. .......................... 128/878; 128/846; 5/623; 602/5; 602/12

(58) Field of Classification Search ................ 128/879, 128/888, 878, 846, 869, 870, 877, 882, 845; 5/646, 647, 600, 603, 623, 624; 602/5, 12
See application file for complete search history.

(56) References Cited

U.S. PATENT DOCUMENTS

| 4,730,801 | A | | 3/1988 | Cloward | |
|---|---|---|---|---|---|
| 5,018,534 | A | * | 5/1991 | Grant | 128/877 |
| 5,020,547 | A | * | 6/1991 | Strock | 128/891 |
| 5,044,025 | A | | 9/1991 | Hunsinger et al. | |
| 5,383,476 | A | | 1/1995 | Peimer et al. | |
| 5,546,963 | A | | 8/1996 | Doody | |
| 5,604,944 | A | | 2/1997 | Meade | |
| 5,609,163 | A | * | 3/1997 | Beard | 128/846 |
| 5,785,057 | A | * | 7/1998 | Fischer | 128/846 |
| 5,827,207 | A | * | 10/1998 | MacMorran | 602/5 |
| 5,832,928 | A | * | 11/1998 | Padilla, Jr. | 128/877 |
| 6,101,650 | A | * | 8/2000 | Omdal et al. | 5/623 |
| 6,298,496 | B1 | | 10/2001 | Evans | |
| 6,298,507 | B1 | | 10/2001 | Clyburn | |
| 6,520,940 | B1 | * | 2/2003 | Gomez | 604/179 |
| 6,553,995 | B1 | | 4/2003 | Cole et al. | |
| 2004/0088774 | A1 | | 5/2004 | Lawson | |
| 2004/0127827 | A1 | | 7/2004 | Fancher | |
| 2005/0091749 | A1 | | 5/2005 | Humbles | |

FOREIGN PATENT DOCUMENTS

WO    WO 01/60440    8/2001

\* cited by examiner

*Primary Examiner*—Patricia M Bianco
*Assistant Examiner*—Ophelia Hawthorne
(74) *Attorney, Agent, or Firm*—Saliwanchik, Lloyd & Saliwanchik

(57) ABSTRACT

The subject invention provides a shield for protecting a patient's extremities when positioned on an arm or leg board or other surgical or examination table extension. The shield comprises essentially an inverted C-shaped or U-shaped covering with a channel therein. It may further comprise one or more flanges to aid in supporting and positioning the shield.

7 Claims, 6 Drawing Sheets

PROTECTIVE SHIELD

CROSS-REFERENCE TO A RELATED APPLICATION

This application claims the benefit of U.S. provisional application Ser. No. 60/749,819, filed on Dec. 13, 2005, which is hereby incorporated by reference in its entirety, including all figures, tables, and drawings.

FIELD OF THE INVENTION

The present invention relates to a shield for protecting portions of a patient's anatomy, for example during surgical or examination procedures.

BACKGROUND OF THE INVENTION

Surgical procedures have evolved into a broad range of different types of operations, with patient positioning depending upon the specific procedure to be accomplished. While most general surgery is performed on a supine patient under the influence of a general anesthetic, other types of surgery require the patient to be positioned in other than a supine position, with hands and arms extended beside or tucked along the side of the patient. An example is the lithotomy position, wherein a patient is generally positioned in a modified supine position with the hips and knees flexed and the legs supported by canvas straps or stirrups, the arms and hands being placed beside the patient, often on arm boards, or loosely cradled over the lower abdomen and secured by the lower end of a blanket. Occasionally the patient may incur injury to the hands through improper positioning of the arms and hands, through pressure when a surgeon leans over and inadvertently bears against the hand, or through crush injuries when the leg portion of the surgical table is raised after the surgery is completed. During surgery a patient is unusually very vulnerable, as the patient is under anesthesia and normal pain warning reactions are blocked.

The bones and other structure of the hands are some of the more fragile components of the human body, and oftentimes inadvertent pressure upon one or both hands, can lead to damage to the hands in the form of a broken bone or pulled tendon, soft tissue, or nerve damage, in addition to transient ischemic problems due to loss of circulation. Such problems are, of course, extremely difficult for a patient, who is often bedridden after surgery and who may have no significant ability to perform any physical act other than with his or her hands and arms. Injury to a patient's hands may deprive the patient of the only other physical activity available until the primary surgical healing process is well underway. Of course, such extra incapacity is a distraction to a positive emotional attitude of the patient during recovery. The cost of inadvertent hand and arm injuries to patients during surgery can be considerable, as the medical profession has a duty of great care during such operations, when the unconscious patient is totally at the mercy of the medical staff performing the procedure.

Accordingly, a need exists for a device which may be used to protect or shield an extremity, such as the hand(s), wrist(s), lower arm(s), leg(s), etc., of a patient who is to experience general anesthesia in order to shield the extremities of the patient from compression or other damage due to inadvertent pressure upon these areas as the patient is positioned prior to, during, and/or after a surgical procedure.

In the past certain devices have been known to locate or position a patient's arm and hand during surgery. For example, U.S. Pat. No. 5,785,057 to Fischer, titled "Medical Positioning Device," describes various embodiments of a device for immobilizing an arm of a surgical patient. The various embodiments each include a downwardly extending flange, with a lateral flange extending inwardly there from. The lateral flange is placed beneath the mattress of a surgical table, to hold the device (and the patient's arm) immobile during surgery. This positioning device is fixed relative to the surgical table.

U.S. Pat. No. 6,101,650 issued Omdal et al., titled "Recessed Arm Board," describes a generally trough shaped device having a squared, U-shaped cross section with a flange extending laterally from the upper edge of one side. The flange is placed beneath the patient or a pad on the operating table with the patient's arm being allowed to rest within the trough. Unfortunately, no padding or upper closure is disclosed to shield a patient's arm from inadvertent pressure.

The foregoing noted limitations regarding previously known surgical hand, wrist and forearm positioning and isolating devices, while significant, demonstrate that room for worthwhile improvement remains.

BRIEF SUMMARY OF THE INVENTION

The present invention provides a novel device for shielding the extremities of a patient from undesirable or unnecessary contact with other objects, for example, the inadvertent leaning of a surgeon or nurse against the extremity during a clinical procedure. The subject invention is particularly useful with surgical or examination tables. More particularly, the subject invention is well-suited for use in shielding the extremities, especially, the hand, arm, elbow and/or upper arm, of a patient, where such extremity is extended, for example across an arm board or similar extension device.

An arm or leg in an extended position, or away from the body, is vulnerable to being bumped, hit, leaned on, or otherwise disturbed, especially in close quarters, for example those that usually exist in an operating or examination room. The subject invention can reduce or eliminate the possibility of injury and/or altering of a patient's one or more extremities in such a position, or any devices or equipment attached thereto.

The subject invention comprises substantially a tubular shield capable of being positioned, in one embodiment, along at least a portion of an arm or leg board or similar extension device. In a further embodiment, the shield of the subject invention further provides a means for attachment to an arm or leg board so that the shield is suspended above and/or around the extended extremity, preferably without touching the extremity or interfering with any equipment or devices attached thereto. In certain embodiments, the tubular shield includes straps or open areas to allow to for easy securement about the patient's extremity.

Accordingly, with the subject extremity shielding device, easy access to a patient's hands or legs for intravenous (IV) administration of medications, for neuromuscular monitoring (such as patient muscle relaxation), or for monitoring other (IV) lines, tubes, or sensors connected to the patient is readily provided. More importantly, the subject shielding device protects the patient's extremities from inadvertent contact with medical personnel (such as nurses, surgeons, anesthesiologists, etc.). For example, when performing operations, the subject shielding device protects the patient's extremities from any pressure that may be exerted from a surgeon's position (i.e., leaning over to make an incision) over the patient.

DETAILED DESCRIPTION OF THE INVENTION

With reference to the attached figures, which show certain embodiments of the subject invention, it can be seen that the shield 10 is in general an elongated inverted C-shaped or U-shaped covering having an uninterrupted channel 19 there through for positioning an extremity, for example an arm or leg. Preferably, the shield 10 has sufficient rigidity or semi-rigidity to protect an extremity therein from undesired contact, such as bumping, pressing, moving, etc.

In one embodiment, shown in the Figures, the shield is a solid covering. However, in other embodiments, the shield covering can have an interrupted channel with various openings therein for diverse purposes, including access to or from various sections of an extremity placed therein, to provide air flow; visibility; contact; positioning/access for straps or tie-downs; access to intravenous lines, tubes, sensors; etc.

Figure 4:
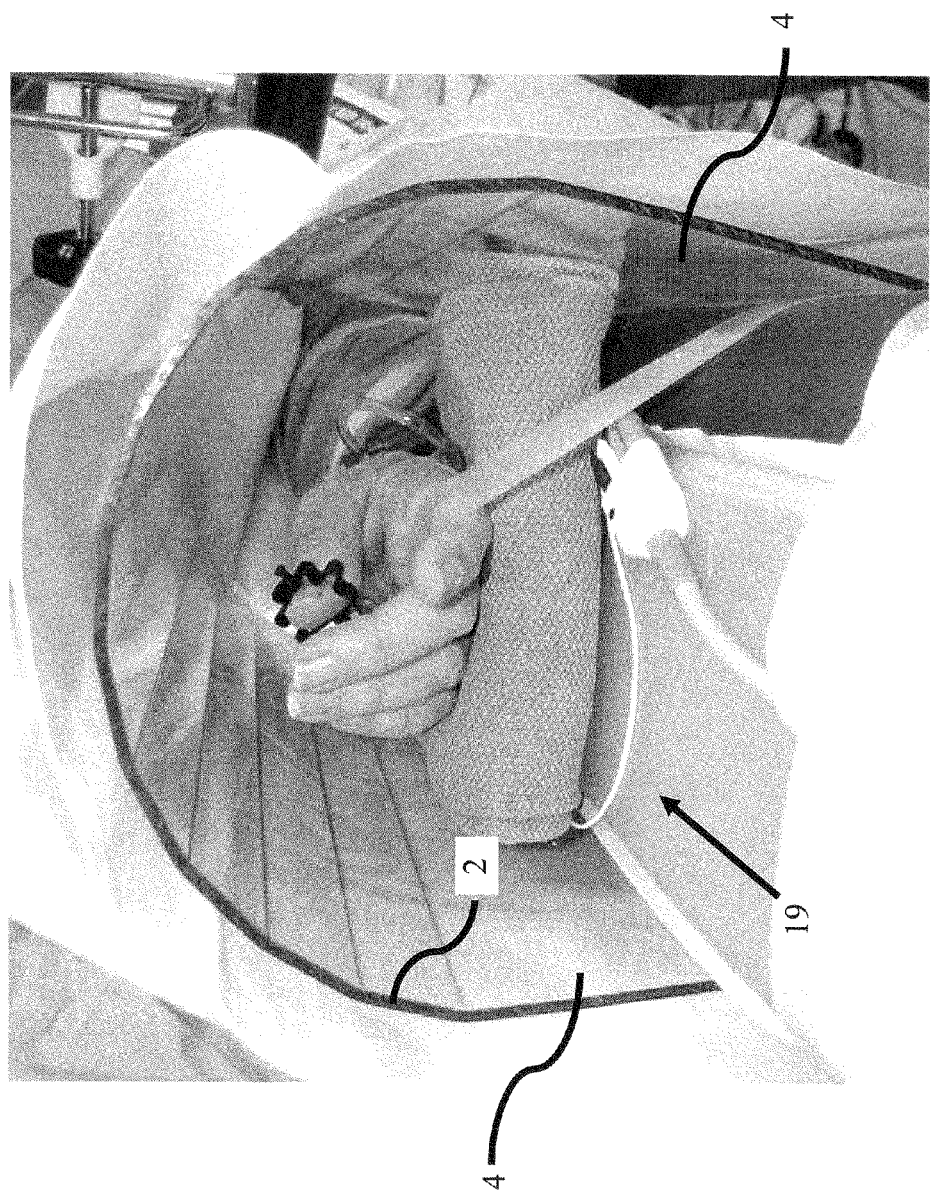
FIG. 4 shows an end view of an embodiment of the subject invention utilized with an arm board of a surgical table.

Alternative embodiments of the invention can include an assortment of support means to lend stability, rigidity and/or strength to the crown 6 and/or sidewalls 4 of the shield. In one embodiment, shown for example in FIGS. 1 and 4, one or more longitudinal support ridges 18 are incorporated into the crown 6. However, a person with skill in the art will recognize that a variety of support means could be utilized with the subject invention, including latitudinal support ridges, embedded supports, structural supports, etc.

The crown 6 of the shield may have any of a variety of circumferential shapes 2, including circular, oval, ovate, squared, triangular, or any other polygonal shape. However, the circumferential shape 2 of the crown 6 should preferably not preclude at least some access to the extremity positioned therein. In other words, the circumferential shape 2 of the crown 6 should allow a person, usually not the patient, to insert their arm or hand into the channel 19 of the shield 10 to manipulate a patient's extremity or equipment or devices attached thereto. The sidewalls 4 of the shield 10 can also determine accessibility to the channel 19, in that, taller sidewalls 4 can provide more height to the shield 10, thus, more space in the channel 19. The sidewalls 4, too, can be of variable shapes, or have openings therein. In a preferred embodiment, the sidewalls 4 are contiguous with the crown 6. However, in an alternative embodiment, the sidewalls 4 are coupled to the crown 6 in a fashion that allows the shield 10 to be fully or partially collapsible. However, in a preferred embodiment the sidewalls 4 are rigidly and fixedly attached to the bottom side 50 of the crown 6.

The base 7 of the shield 10 may comprise a continuous panel that joins the ends of the sidewalls 4 along the bottom side 50 of the shield 10. In this embodiment, the shield 10 can be positioned around a patient's extremity to be protected, as well as an extension device, such as an arm or leg board of a surgical or examination table, by sliding it sleeve-like over the end of the extension device and patient extremity so that it covers a desired length or portion of the extension and extremity. In this embodiment, the sidewalls 4 press against the sides of the extension device so that pressure between the sidewalls 4 and the edges of an extension device help to maintain the position of the shield 10 over an extremity.

Alternatively, the base 7 of the shield 10 can be placed or sat on top of a support board 25 (such as an extension device, or any other surface for supporting a patient's limb), and an extremity inserted therein or an extremity can be inserted therein and the base of the shield placed on top of a support board 25 (such as an extension device). The weight of the extremity and any other support or cushioning contained in the channel 19 of the shield 10 used can assist in holding the shield 10 in place.

Figure 5:
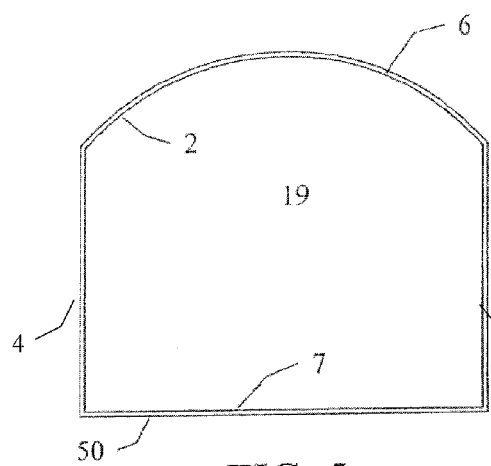
FIG. 5 shows a front view of an embodiment of the subject invention having a solid base.

In a related embodiment, the base 7 of the shield 10 can be secured to the top of the support board 25 (i.e., extension device) by other means known in the art. An example of this shield embodiment is shown in the diagram of FIG. 5.

In a still further alternative to this embodiment, the base 7 may be a variety of shapes from flat to diverse curves or angles to accommodate specific extremities in a medical or even veterinary use. Further, the base 7 of this embodiment can have one or more openings or holes therein. These openings may provide access to or away from an extremity, a means for securing the shield 10 to a surface, air flow, etc.

Figure 1:
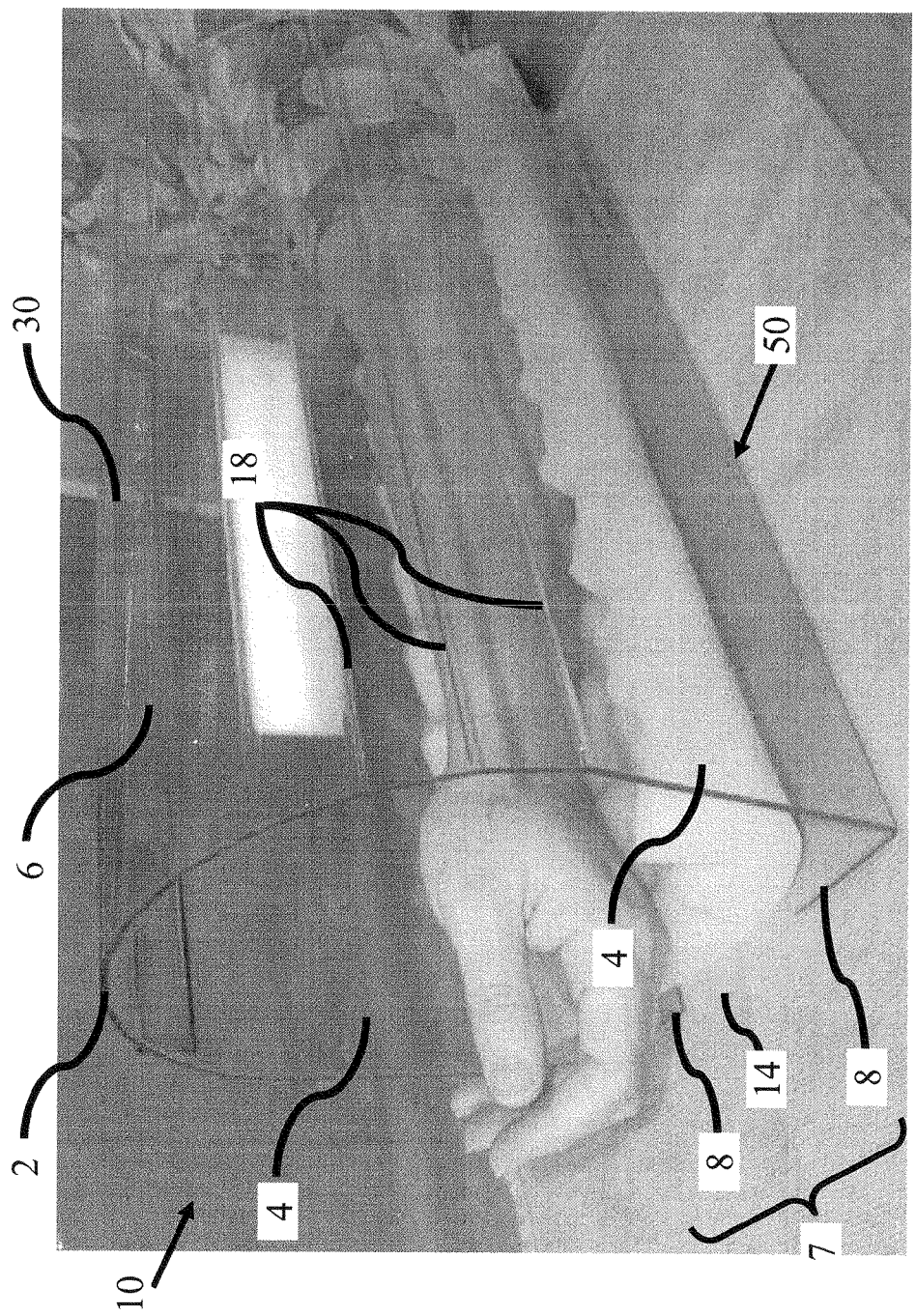
FIG. 1 shows a perspective view of an embodiment of the subject invention.
Figure 6:
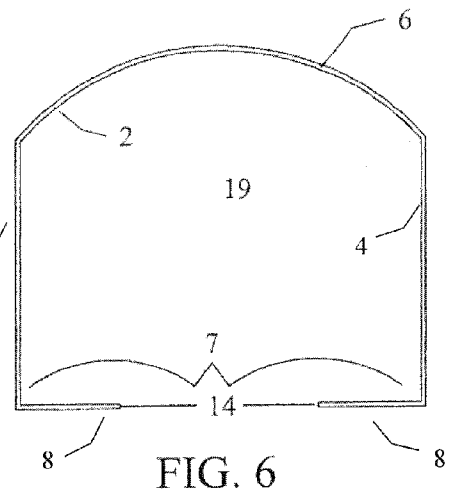
FIG. 6 shows a front view of an embodiment of the subject invention having two flanges.

In a preferred embodiment, the base 7 of the shield 10 comprises a longitudinal notch 14 that dissociates the sides of the shield 10 and provides at least one longitudinal flange 8 protruding essentially perpendicular from the bottom 50 end of at least one of the sidewalls 4. In a further preferred embodiment, there are provided at least two flanges protruding essentially perpendicular from the bottom 50 end of the sidewalls 4. In these embodiments, the at least one, and preferably two, flanges 8 project essentially towards the center of the base 7, for example as shown in FIGS. 1 and 6. In a further embodiment, the flanges may be coupled to the sidewalls 4 in a fashion that allows the flanges 8 to be fully or partially collapsible. For example, the flanges 8 could be hingedly connected to the sidewalls 4. However, in a preferred embodiment, the one or more flanges 8 are rigidly and fixedly attached to the bottom end(s) 50 of the sidewalls 4.

In this preferred embodiment, the shield 10 can be affixed to an arm or leg board, or other type of surgical or examination table extension, by one of two methods. In the first method, as described above, the shield 10 can be positioned over an extension by sliding it over the end of an extension so that it covers a desired length of the extension. In this embodiment, the sidewalls 4 press against the sides of the extension so that pressure between the sidewalls 4 and the edges of an extension help to maintain the position of the shield 10 over an extremity.

However, in a preferred method, the shield is placed over an extension by manually stretching apart the walls of the shield 10 to sufficiently go over the sides of the extension. This may be accomplished by a variety of means by either one or two people. By way of example, the one or more flanges 8 on a first sidewall 4 of the shield 10 can be placed over one side of an extension so that the one or more flanges are against the underside of the extension and the sidewall 4 is pressed firmly against the side edge of the extension. Then, by firmly holding the second or opposite sidewall 4 of the shield the sidewalls 4 can be pulled apart enough to allow the second sidewall 4 and the flange 8 thereon to go over the opposite side of the extension. Once the second sidewall 4 and flange 8 are placed, the walls can be allowed to return to an original position so that the pressure of the sidewalls 4 on the sides edges of the extension maintain the position of the shield 10 over desired length of the extension.

For this method of attachment, the crown 6 and sidewalls 4 of the shield 10 should have a sufficient amount of flexibility to accommodate stretching and/or flexing of these shield 10 elements, but enough rigidity and material memory to return to the original position so that the shield can be held in place around an extension device.

Figure 7:
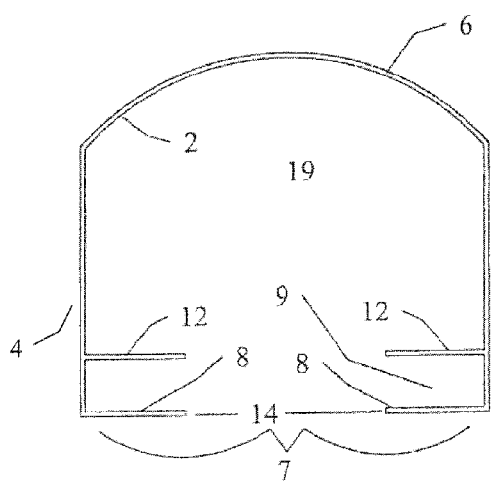
FIG. 7 shows a front view of an embodiment of the subject invention having bottom and top flanges.
Figure 8:
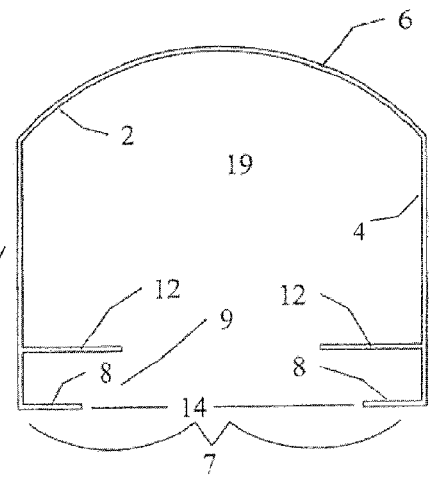
FIG. 8 shows a front view of an embodiment of the subject invention having bottom and top flanges of different lengths.
Figure 9:
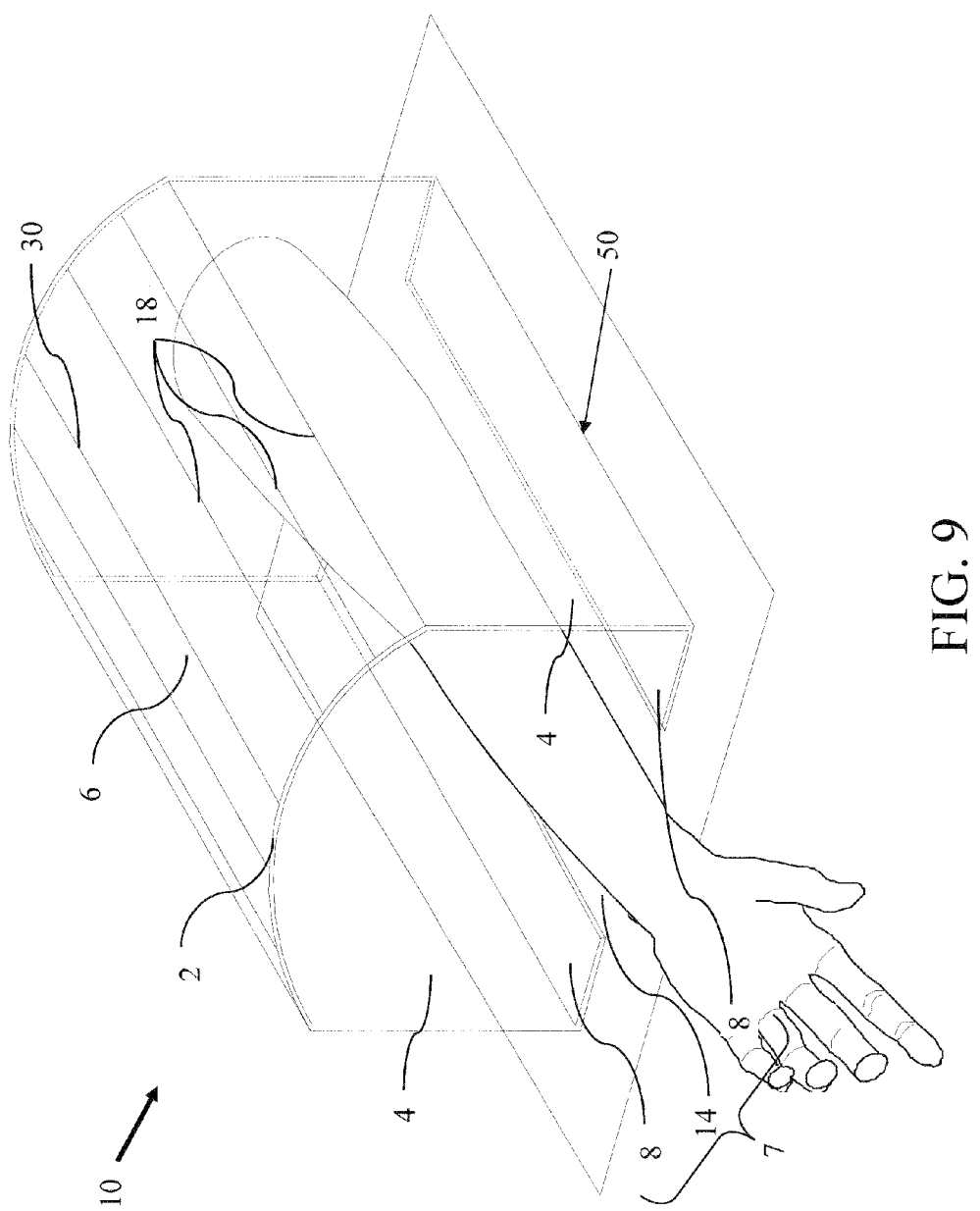
FIG. 9 shows a perspective view of an embodiment of the subject invention, the same view as the photograph in FIG. 1.

In another alternative embodiment one or more top flanges 12 parallel to the one or more of the flanges 8 may be utilized to secure the shield to an arm board, leg board or other surgical or examination table extension. When affixed to an extension as described above, a top flange 12 could be positioned on the upper side of the extension, parallel to the flange 8 which is positioned on the underside of the extension. Thus, the board or other extension would be positioned in one or more flange channels 9, for example as shown in FIGS. 7 and 8. In a further alternative embodiment, the one or more top flanges 12 may be a different length, for example they could be longer than the flanges 8 to aid in placement against the upper side of an extension. An example of this shield embodiment is shown in the diagram in FIG. 8. The use of one or more top flanges 12 can assist in positioning the shield 10 over a board or extension, and, further, can reduce or prevent the shield from being moved out of position, particularly if the shield is pushed from the top side 30, or even if the sidewalls 4 are bumped, pushed, etc.

Figure 2:
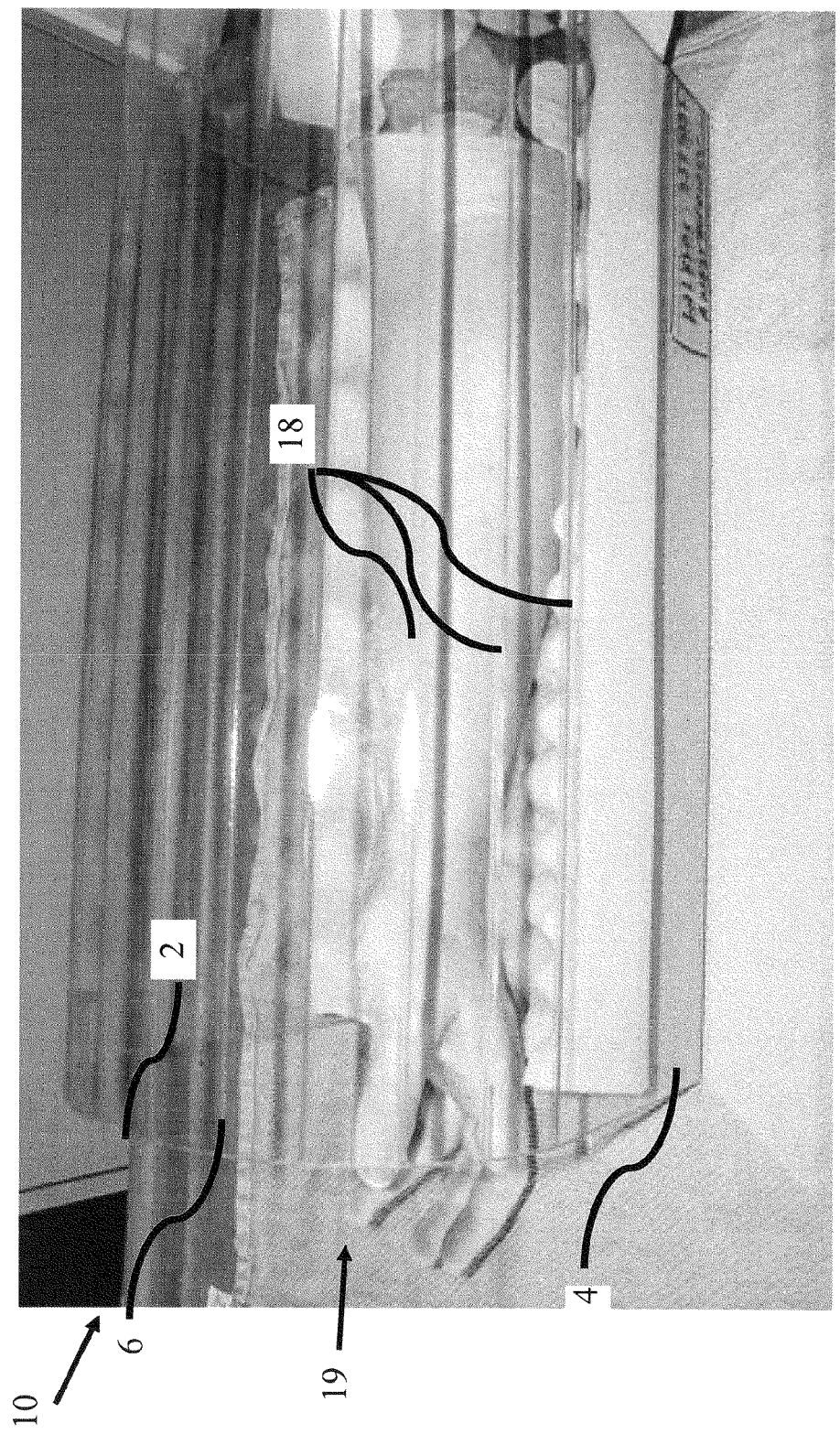
FIG. 2 shows a side view of an embodiment of the subject invention.
Figure 3:
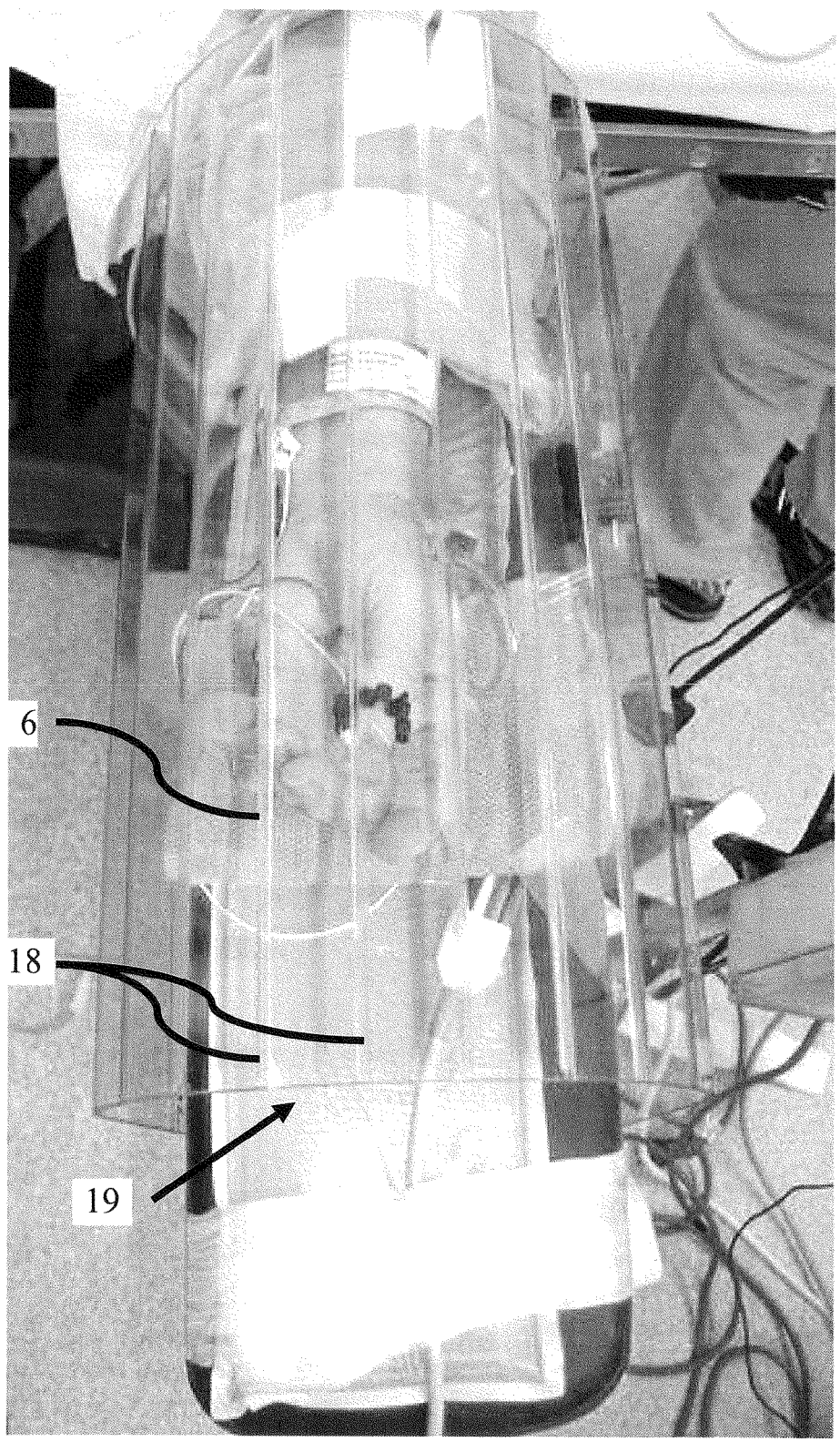
FIG. 3 shows a top view of an embodiment of the subject invention utilized with an arm board of a surgical table.

A person with skill in the art will recognize that various alternative devices may also be utilized with the shield embodiments discussed above. For example, various cushions, pads, or other comfort or positioning devices can be used to facilitate the comfort or correct positioning of a patient. These devices can be incorporated as part of the shield device, or can be separate components that the shield is able to surround, for example as shown in FIGS. 2 and 3.

It may also be desirable to utilize various securing means with the shield to maintain positioning of an extremity within the shield. For example, straps or other securing means can be affixed to the sidewalls 4 of the shield 10 which could be used to position and hold an extremity in a particularly desirable position within the shield. A wide variety of other devices useful for maintaining the comfort or positioning of a patient with the subject invention will be apparent to those skilled in the art from the description provided herewith.

Further alternative embodiment may utilize various means for securing the shield 10 to an extension device. By way of example, VELCO™ could be used between the base 7 of the shield 10 and the extension device to secure the position of the shield 10, but ensure easy removal if/when necessary. In addition, latches, straps, tie-downs, or other devices known to those with skill in the art could be utilized to secure the position of the shield 10 on or around an extension device.

The shield may comprise a variety of materials including glass, plastics, acrylics, plexiglass, wood, rubber, metals, paper products, etc. or combinations thereof. In one embodiment, the shield comprises a plexiglass, or similar material, with sufficient tension strength to provide protection, but enough resiliency to allow placement of the shield over an arm or leg board or other type of extension, as described above.

Where the shield is transparent, it may be composed of materials of transparent lightweight synthetic resinous plastic such as polycarbonate, polypropylene, polyethylene, polyvinyl chloride, or the like. Preferably it has a thickness between about 0.01 inch to 1.00 inch. In a more preferred embodiment, the shield is made of a clear polycarbonate (such as ⅜" GE-LEXAN®) that is lightweight and has high stiffness, easy workability, and is impact resistant.

Further, the shield may comprise any variety or combination or colors and be opaque or clear or numerous shades or combinations in between. In a preferred embodiment, the shield 10 is clear, or semi-clear, but a person with skill in the art would recognize that the environment of intended use can dictate the clarity or color of the shield.

In addition, the overall dimensions of the shield can vary depending upon intended use. For example, the length of the shield can vary depending upon whether it would be desirable to cover a full forearm and hand, or the entire arm. Alternatively, if used for protecting a larger extremity, it may be desirable to have a longer shield with a slightly wider channel 19. For example, a shield for covering the forearm and hand of a human patient may be approximately 12 inches to about 17 inches in length and be approximately 8 inches to about 12 inches in height. In a preferred embodiment, the shield is approximately 15 inches in length and 8 inches in height to the top of the crown circumference. In a most preferred embodiment, the shield is approximately 15 inches in length and 10 inches in height with a circular crown circumference of approximately a 5-7 inch radius.

The thickness of the shield will depend upon the type of material(s) utilized in its construction. As discussed above, a preferred method of operation includes separating the sidewalls 4 of the shield 10, causing the crown 6 to bend or bow. Thus, the materials utilized in the manufacture of the shield 10 should accommodate sufficient bending or bowing to install the shield over an arm or leg board or other surgical or examination table extension by this method. Another consideration is overall weight of the shield. It is preferable for the shield to be as lightweight as possible, but still provide sufficient rigidity to protect an extremity therein. Thus, lighter materials for example, but not limited to, plexiglass, acrylics, plastics, etc., might be preferable. If these, or similar, materials are utilized, the overall thickness may range from about 1/16" to about ½" in thickness. Certain metals may also be applicable to the subject invention, for example, aluminum, steel, various metal composites, etc.

Following is an example that illustrates procedures for practicing the invention. This example should not be construed as limiting. All measurements are in inches unless stated otherwise.

EXAMPLE 1

In this embodiment the shield of the subject invention comprises a clear or semi-clear plexiglass material approximately ¼" thick. The length of the shield is about 15". The crown circumference is circular having a radius of about 6" which provides an overall width of about 12". The height of the shield from the base to the top of the crown circumference is about 10 inches.

The base of the shield is bisected by a notch approximately 6" wide. Further, each sidewall has fixedly connected thereto a flange that extend towards the center of the base of the shield. The flange extends along the bottom edge of the sidewalls and is contiguous with the side wall.

In operation, this shield embodiment is installed, preferably, over a support board 25 (such as an arm or leg board or other surgical or examination table extension) by first placing one flange over an edge of the support board 25 so that it rests against the underside of the support board 25 and, at the same time, the sidewall to which it is attached is pressed against the side or edge of the support board 25. The second sidewall may then be pulled away from the first sidewall, increasing the space between the sidewalls until the flange on the second sidewall can then be lowered over the opposite side or edge of the support board 25. Then, by slowly releasing pressure on the second sidewall, the shield can be held in place by the pressure of the sidewalls pressing against the edges of the support board 25.

All patents, patent applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A method for protecting an extremity utilizing a shield device comprising a covering such that a rigid or semi-rigid tubular channel is formed therethrough, wherein said covering comprises:
    a crown having a circumferential shape, wherein the crown is provided over an entire length of the channel;
    a first sidewall fixedly attached at one end to the crown;
    a second sidewall opposite the first sidewall and fixedly attached at one end to the crown; and
    a base comprising a first flange fixedly attached to the first sidewall at or near an end opposite the crown and provided along the entire length of the channel, and a second flange fixedly attached to the second sidewall at or near an end opposite the crown and provided along the entire length of the channel; wherein the first flange projects, from the first sidewall, towards the second flange; and wherein the second flange projects, from the second sidewall, towards the first flange; and wherein the base further comprises a longitudinal notch between the first flange and the second flange,
said method comprising,
    placing the first flange over a first edge of a support board utilizing the longitudinal notch, such that the first sidewall is positioned against the support board and the first flange is positioned under the support board;
    applying pressure to the second sidewall to increase the distance between the first sidewall and the second sidewall until the second flange on the second sidewall can be positioned over a second edge of the support board,
    decreasing pressure to the second sidewall until it is positioned against the second edge of the support board and the second flange is positioned under the second edge of the support, such that the pressure of the first and second sidewalls against the first and second edges of the support board assists in maintaining the position of the shield device; and
    positioning a patient extremity, or a portion thereof, within the channel, such that the extremity is generally resting on the support board and covered by the shield device.

2. The method according to claim 1, wherein the extremity is positioned on the support board prior to the shield device being positioned on the support board.

3. The method, according to claim 1, wherein the shield device is placed on top of the support board.

4. The method, according to claim 1, wherein said shield device further comprises one or more straps to secure the shield device to the support board, said method further comprising securing the shield device to the support board using the strap(s).

5. A method for protecting an extremity utilizing a shield device comprising a covering such that a rigid or semi-rigid tubular channel is formed therethrough, wherein said covering comprises:
    a crown having a circumferential shape, wherein the crown is provided over an entire length of the channel;
    a first sidewall fixedly attached at one end to the crown;
    a second sidewall opposite the first sidewall and fixedly attached at one end to the crown; and
    a base comprising a first flange fixedly attached to the first sidewall at or near an end opposite the crown and provided along the entire length of the channel, and a second flange fixedly attached to the second sidewall at or near an end opposite the crown and provided along the entire length of the channel; wherein the first flange projects, from the first sidewall, towards the second flange; and wherein the second flange projects, from the second sidewall, towards the first flange; and wherein the base further comprises a longitudinal notch between the first flange and the second flange,
said method comprising,
    sliding the shield device over one end of a support board, causing the first and second sidewalls to simultaneously separate sufficiently to properly place the shield device on the support board, where edges of the support board provide adequate pressure against the first and second sidewalls of the shield device to maintain the position of the shield device on the support board; and
    positioning a patient extremity, or a portion thereof, within the channel, such that the extremity is generally resting on the support board and covered by the shield device.

6. The method, according to claim 5, wherein the extremity is positioned on the support board prior to sliding the shield device on the support board.

7. The method, according to claim 5, wherein said shield device further comprises one or more straps to secure the shield device to the support board, said method further comprising securing the shield device to the support board using the strap(s).

* * * * *